US011698612B2

United States Patent
Alexander et al.

(10) Patent No.: US 11,698,612 B2
(45) Date of Patent: Jul. 11, 2023

(54) EXTENSION CORD

(71) Applicant: FNA Group, Inc., Pleasant Prairie, WI (US)

(72) Inventors: Chris Alexander, Park Ridge, IL (US); Richard J. Gilpatrick, Burlington, WI (US)

(73) Assignee: IMPACT CONSULTING AND ENGINEERING LLC, Naples, FL (US)

( * ) Notice: Subject to any disclaimer, the term of this patent is extended or adjusted under 35 U.S.C. 154(b) by 379 days.

(21) Appl. No.: 16/865,745

(22) Filed: May 4, 2020

(65) Prior Publication Data

US 2020/0348639 A1 Nov. 5, 2020

Related U.S. Application Data

(60) Provisional application No. 62/841,959, filed on May 2, 2019.

(51) Int. Cl.
| | | |
|---|---|---|
| *G05B 19/042* | (2006.01) | |
| *G01R 21/00* | (2006.01) | |
| *G08B 21/18* | (2006.01) | |
| *G08B 21/14* | (2006.01) | |

(Continued)

(52) U.S. Cl.
CPC ......... *G05B 19/042* (2013.01); *G01R 21/007* (2013.01); *G08B 21/14* (2013.01); *G08B 21/182* (2013.01); *G01N 33/004* (2013.01); *G05B 2219/2639* (2013.01); *G06Q 50/06* (2013.01)

(58) Field of Classification Search
CPC ............ G05B 2219/2639; G06Q 50/06; G08B 21/14; G08B 21/18
See application file for complete search history.

(56) References Cited

U.S. PATENT DOCUMENTS 4,097,843 A * 6/1978 Basile ................. G08B 21/185
340/687
5,418,521 A * 5/1995 Read .................. G08B 13/1409
340/687

(Continued)

FOREIGN PATENT DOCUMENTS

TW 201032423 A * 9/2010
WO WO-2012128912 A2 * 9/2012 ............. G01R 21/00

*Primary Examiner* — Vincent H Tran
(74) *Attorney, Agent, or Firm* — Brian J. Colandreo; Jeffery T. Placker; Holland & Knight LLP

(57) ABSTRACT

An extension cord includes a plurality of electrical conductors. A plug is configured to electrically couple a first respective end of the plurality of electrical conductors with an electrical receptacle of a power source. An outlet assembly is coupled with a second respective end of the plurality of electrical conductors. The outlet assembly may include one or more outlet receptacles configured to provide electrical power from the power source. A power meter may be configured to measure an electrical draw through the outlet assembly and to provide a user perceptible output based upon the measured electrical draw. A carbon monoxide monitor may be configured to detect an environmental carbon monoxide level proximate the outlet assembly and to provide a user perceptible indication when the detected environment carbon monoxide level exceeds a threshold.

16 Claims, 6 Drawing Sheets

(51) Int. Cl.
*G01N 33/00* (2006.01)
*G06Q 50/06* (2012.01)

(56) References Cited

U.S. PATENT DOCUMENTS

| | | | | |
|---|---|---|---|---|
| 5,663,711 | A * | 9/1997 | Sanders | G08B 21/185 |
| | | | | 340/654 |
| 7,209,048 | B1 * | 4/2007 | Pace | H01R 13/652 |
| | | | | 340/687 |
| 7,540,767 | B1 * | 6/2009 | Czarnecki | H01R 25/003 |
| | | | | 439/502 |
| 9,419,417 | B1 * | 8/2016 | Taxter | H01R 24/76 |
| 2003/0125886 | A1 * | 7/2003 | Spitaels | H02J 3/14 |
| | | | | 702/62 |
| 2008/0120048 | A1 * | 5/2008 | Zhou | H02H 3/42 |
| | | | | 702/60 |
| 2008/0182215 | A1 * | 7/2008 | Sid | G01N 33/004 |
| | | | | 431/18 |
| 2008/0279343 | A1 * | 11/2008 | Bentley | H04M 1/21 |
| | | | | 379/33 |
| 2009/0230950 | A1 * | 9/2009 | Czarnecki | H01R 25/003 |
| | | | | 324/142 |
| 2013/0314069 | A1 * | 11/2013 | Suzuki | H02J 50/80 |
| | | | | 323/318 |
| 2014/0068486 | A1 * | 3/2014 | Sellers | H04L 12/2818 |
| | | | | 715/771 |
| 2014/0088779 | A1 * | 3/2014 | Chen | G06F 1/266 |
| | | | | 700/295 |
| 2017/0328877 | A1 * | 11/2017 | Bajaj | G01N 33/0075 |
| 2018/0050230 | A1 * | 2/2018 | Toland | H04M 1/72409 |
| 2020/0036310 | A1 * | 1/2020 | Sarder | G01N 33/004 |
| 2020/0309825 | A1 * | 10/2020 | Arredondo | G01R 19/16547 |

* cited by examiner

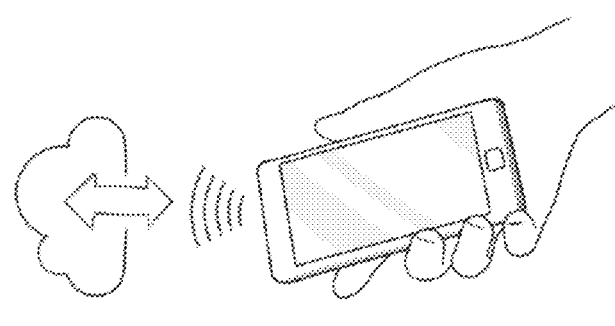
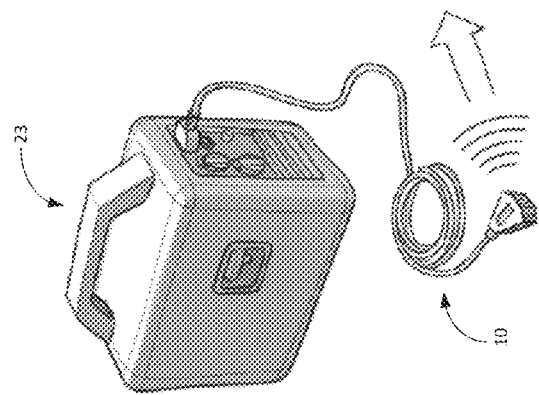
FIG. 5

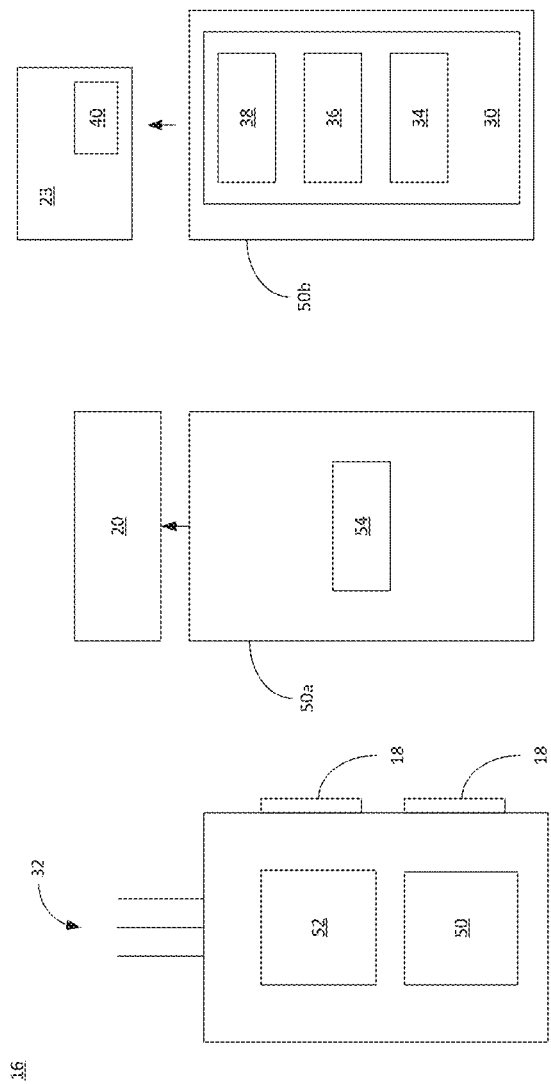

EXTENSION CORD

CROSS-REFERENCE TO RELATED APPLICATIONS

This applications claims the benefit of U.S. provisional application Ser. No. 62/841,959 entitled "Smart Cord," filed on 2 May 2019, the entire contents of both of which are incorporated herein by reference.

TECHNICAL FIELD

The present invention generally relates to extension cords, and more particularly relates to extension cords suited for use with portable generators.

BACKGROUND

In general, an engine driven generator may include a prime mover (such as an internal combustion engine) drivingly connected to an electric generator for providing electrical power. Conventionally, engine driven generators may be used in a variety of circumstances to provide electrical power when it may not otherwise be available or conveniently accessed. For example, engine driven generators may be used at jobsites and/or worksites at which electrical power may not be conveniently available due to remoteness of the jobsite, because electrical service has not yet been established at the jobsite, etc. Engine driven generators may also often be used as back-up generators to provide electricity during power outages. Engine driven generators may similarly be used in a variety of different and/or additional applications.

The manner in which electricity from an engine driven generator may vary depending upon, for example, the size and the intended use of the engine driven generator. For example, many larger engine driven generators may be hardwired into the electrical service of a home or building. Engine driven generators known as portable generators, may typically include one, or even several, electrical receptacles integrated into a control panel, housing, or chassis of the generator. As such, electrical devices may be directly plugged into the receptacles included on the portable generator. In some circumstances, the noise and exhaust fumes emitted by the internal combustion engine may make is less desirable to plug device directly into a portable generator, for example, because doing so may require a user to be in relatively close proximity to the portable generator while the electrical device is in use.

SUMMARY

According to an implementation, an extension cord may include a plurality of electrical conductors. A plug may be configured to electrically couple a first respective end of the plurality of electrical conductors with an electrical receptacle of a power source. An outlet assembly may be coupled with a second respective end of the plurality of electrical conductors. The outlet assembly may include one or more outlet receptacles configured to provide electrical power from the power source. The outlet assembly may further include a power meter configured to measure an electrical draw through the outlet assembly.

One or more of the following features may be included. The power source may include a portable generator. The plug may include one or more of a NEMA 5-15 plug, a NEMA 5-20 plug, a NEMA L14-30 plug, a 12 VDC power port plug, and a USB plug. The one or more outlet receptacles may include one or more of NEMA 5-15 receptacle, a NEMA 5-20 receptacle, a NEMA L14-30 receptacle, a 12 VDC power port socket, and a USB port.

The power meter may be configured to measure one or more of a current draw through the outlet assembly and a power draw through the outlet assembly. The outlet assembly may further include a draw indicator providing a user perceptible indicator of the measured one or more of the current draw through the outlet assembly and the power draw through the outlet assembly. The user perceptible indicator may include one or more of a visual indicator and an auditory indicator. The user perceptible indicator may be based upon, at least in part, a maximum service power associated with the plug. The user perceptible indicator may provide at least an indication that the electrical draw through the outlet assembly is approaching a maximum service rating associated with the plug.

The outlet assembly may further include a carbon monoxide monitor. The carbon monoxide monitor may be configured to detect an environmental carbon monoxide level proximate the outlet assembly. The carbon monoxide monitor may be configured to provide an alert when the detected environmental carbon monoxide level proximate the outlet assembly exceeds a threshold level.

According to another implementation, an extension cord may include a plurality of electrical conductors. A plug may be configured to electrically couple a first respective end of the plurality of electrical conductors with an electrical receptacle of a power source. An outlet assembly may be coupled with a second respective end of the plurality of electrical conductors. The outlet assembly may include one or more outlet receptacles configured to provide electrical power from the power source. The outlet assembly may further include a carbon monoxide monitor configured to detect an environmental carbon monoxide level proximate the outlet assembly.

One or more of the following features may be included. The power source may include a portable generator. The plug may include one or more of a NEMA 5-15 plug, a NEMA 5-20 plug, a NEMA L14-30 plug, a 12 VDC power port plug, and a USB plug. The one or more outlet receptacles may include one or more of NEMA 5-15 receptacle, a NEMA 5-20 receptacle, a NEMA L14-30 receptacle, a 12 VDC power port socket, and a USB port.

The carbon monoxide monitor may be configured to provide an alert when the detected environmental carbon monoxide level proximate the outlet assembly exceeds a threshold level. The outlet assembly may include one or more of a visual alert unit and an audible alert unit for providing the alert when the detected environmental carbon monoxide level exceeds the threshold level.

The power source may include a portable generator. The carbon monoxide monitor may be operatively coupled with the portable generator to shut down an engine associated with the portable generator when the detected carbon monoxide level exceeds the threshold level. The carbon monoxide monitor may be communicatively coupled with a control system of the portable generator to shut down the engine.

The outlet assembly may further include a power meter configured to measure an electrical draw through the outlet assembly. The power meter may provide a user perceptible indication based upon the measured electrical draw.

According to yet another implementation, an extension cord may include a plurality of electrical conductors. A plug may be configured to electrically couple a first respective end of the plurality of electrical conductors with an electrical receptacle of a power source. An outlet assembly may be coupled with a second respective end of the plurality of electrical conductors. The outlet assembly may include one or more outlet receptacles configured to provide electrical power from the power source. The outlet assembly may include a power meter configured to measure an electrical draw through the outlet assembly and configured to provide a user perceptible output based upon the measured electrical draw. The outlet assembly may include a carbon monoxide monitor configured to detect an environmental carbon monoxide level proximate the outlet assembly. The carbon monoxide monitor may be configured to provide a user perceptible indication when the detected environment carbon monoxide level exceeds a threshold.

BRIEF DESCRIPTION OF THE DRAWINGS

FIG. 5 depicts an illustrative example of an extension cord consistent with the present disclosure including a twist-lock plug, and including wireless communication, consistent with an example embodiment;

FIG. 6 schematically depicts an illustrative example of an outlet assembly, consistent with an example embodiment;

FIG. 7 schematically depicts an illustrative example of a controller, consistent with an example embodiment; and FIG. 8 schematically depicts another illustrative example of a controller, consistent with an example embodiment.

DETAILED DESCRIPTION

In general, the present disclosure may provide an extension cord providing various safety and/or convenience features. In some particular embodiments, the present disclosure may provide an extension cord that may be particularly suited for use in connection with a power source, such as a generator, including, but not limited to, a portable generator. Consistent with some such illustrative example embodiments, various electrical devices may be powered by the portable generator (or other power source) via the extension cord, e.g., which may allow greater separation between the electrical devices and the generator than may be possible with the electrical cords of the electrical devices alone. Further, consistent with the present disclose, the extension cord may provide various safety and/or convenience features. For example, in some illustrative example embodiments, the extension cord may include a power meter at an outlet end of the extension cord that may provide an indication of the power being consumed by electrical devices plugged into the generator via the extension cord. In some illustrative example embodiments, the extension cord may include a carbon monoxide monitor that may detect and/or measure a carbon monoxide level at the outlet end of the extension cord. Further, in some illustrative example embodiments, various combinations of safety and/or convenience features (including, but not limited to, a power meter, a carbon monoxide monitor, and/or additional or alternative features) may be associated with an extension cord consistent with the present disclosure.

Figure 1:
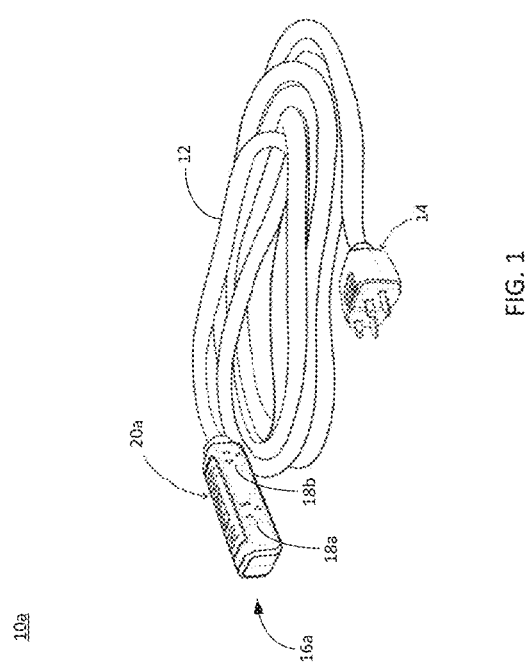
FIG. 1 depicts an illustrative example of an extension cord, consistent with an example embodiment.
Figure 2:
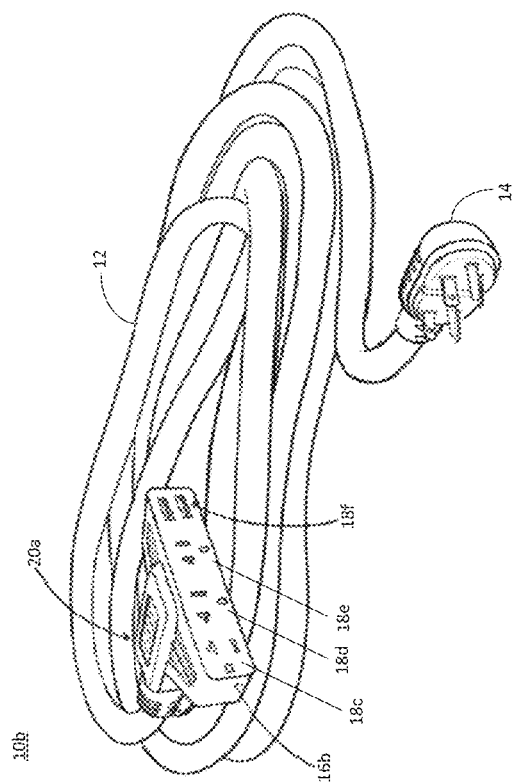
FIG. 2 depicts another illustrative example of an extension cord, consistent with an example embodiment.

For example, and referring to FIGS. 1 and 2, illustrative example embodiments of an extension cord (e.g., extension cords 10a, 10b, which may also be generally referenced as "extension cord 10" when common and/or interchangeable features of the extension may be discussed) consistent with the present disclosure is generally shown. As shown, the extension cord 10 may generally include a plurality of electrical conductors (e.g., which may be disposed within an protective jacket 12). The extension cord 10 may include plug 14 that may be configured to electrically couple a first respective end of the plurality of electrical conductors with an electrical receptacle of a power source. The extension cord 10 may also include an outlet assembly 16 that may be coupled with a second respective end of the plurality of electrical conductors. The outlet assembly 16 may include one or more outlet receptacles (e.g., outlet receptacles 18a, 18b, 18c, 18d, 18e, 18f) configured to provide electrical power from the power source. Consistent with the illustrated example embodiment, the outlet assembly 16 may further include a power meter (e.g., power meters 20a, 20b, which may also generally be referred to as "power meter 20" when common and/or interchangeable features of the power meter may be discussed), configured to measure an electrical draw through the outlet assembly 16.

As discussed above, in an illustrative example embodiment, the extension cord 10 may include a plurality of electrical conductors. As shown, and as is generally known, the plurality of conductor may be disposed within the protective jacket 12. Generally, each of the plurality of electrical conductors may include a wire (either solid or stranded), typically, but not necessarily copper wires. The plurality of conductions may be of an appropriate wire gauge for a designed current rating (e.g., 12 gauge for a 20 amp design load, 10 gauge for a 30 amp design load, etc.) It will be appreciated that the other wire gauges and design loads may be equally utilized. Additionally, and as will be further discussed below, the number of electrical conductors may vary, e.g., depending upon the configuration of the plug 14 and the outlet assembly 16. For example, the extension cord may include a hot conductor, a neutral conductor, and a ground conductor. In some embodiments, the extension cord may include more than one hot conductor, more than one neutral conductor, and/or more than one ground conductor. Further, in some embodiments, one or more additional and/or alternative electrical conductors may be included. It should be understood that the designation "hot," "neutral," and "ground" are intended to correlate to common terminology associated with alternating current electrical systems, and are intended for descriptive purposes only, and should not be construed as a limitation on the role or characteristics of the electrical conductors. Consistent with some embodiments, the protective jacket 12 may include an outdoor rated jacket/insulation that may be suitable for use in outdoor and/or wet locations. According to such embodiments, the extension cord may be suitable for outdoor usage over extended period of time. In some embodiments, the protective jacket may not be outdoor rated. Further, as is generally known, in addition to the protective jacket, one or more of the plurality of electrical conductors may also be individually insulated. The electrical conductors (and the protective jacket 12) may be selected to provide the extension cord 10 having any desired length. For example, in some embodiments the extension cord may have a length of between 20 feet and 30 feet. In other embodiments, the extension cord may have other desired lengths, such as 50 feet, etc. It will be appreciated that the length of the extension cord may vary based on various design considerations and preferences.

As noted above, the plug 14 may be configured to electrically couple a first respective end of the plurality of electrical conductors with an electrical receptacle of a power source. For example, and as shown, the plug 14 may include a plurality of contacts that may each be electrically coupled to a first end of a respective electrical conductor. The plurality of contacts (e.g., which, as is generally known, may include blades or other suitable contacts) may be arranged to mechanically and electrically couple with cooperating contacts of an electrical receptacle associated with the power source. In a similar manner as the protective jacket 12, in some embodiments the plug 14 may include an outdoor rated plug, e.g., which may provide improved weather and environmental protection (e.g., as compared to a plug that is not outdoor rated). In other embodiments, the plug may not be outdoor rated. Consistent with various embodiments, the plug may include a variety of configurations, e.g., which may be suitable for mechanically and/or electrically coupling with various different receptacle configurations. For example, in some embodiments, the plug 14 may include, but is not limited to, one or more of a NEMA 5-15 plug, a NEMA 5-20 plug, a NEMA L14-30 plug, a 12 VDC power port plug, and a USB plug.

In some embodiments, the plug may include electrical contacts that may be configured to mechanically and/or electrically couple with one or more different receptacles, either simultaneously and/or alternatively. For example, as is generally known, a NEMA 5-15 plug may be capable of mechanically and electrically coupling with either a NEMA 5-15 receptacle and a NEMA 5-20 receptacle. As will be appreciated, and as shown in the illustrated example embodiments, the plug (as well as any housing and/or plug body) may take a variety of configurations, which may vary according to design criteria and preference. Further, in some embodiments the plug 14 may be capable of being simultaneously coupled with more than on receptacle. For example, and as shown in the illustrative example embodiments of FIGS. 1 and 2, the plug 14 may include a duplex plug configuration that is configured to be simultaneously coupled with two receptacles arranged in a duplex configuration. In some such embodiments, the extension cord may include a plurality of electrical conductors configured to be electrically coupled with each of the contacts of the plug (e.g., including all six of the electrical contacts in the illustrated example embodiment of a duplex plug). In other embodiments, electrical conductors may only be provided corresponding to a portion of the electrical contacts. For example, in an example embodiment a single hot conductor may be electrically coupled to the two hot contacts of the duplex plug, a single neutral conductor may be electrically coupled to the two neutral contacts of the duplex plug, and a single ground conductor may be electrically coupled to the two ground contacts of the duplex plug. In still a further example embodiment, electrical conductors may only be provided associated with a portion of the contacts. For example, a single hot conductor may be electrically coupled to the hot contact of a first portion of the duplex plug, a single neutral conductor may be electrically coupled to the neutral contact of the first portion of the duplex plug, and a single ground conductor may be electrically coupled to the ground contact of the first portion of the duplex plug. In some such embodiments, the second portion of the duplex plug may be provided, e.g., to prevent an additional plug being electrically coupled with a second portion of a duplex receptacle of the power source, which may limit the power draw through the duplex receptacle to devices plugged into the extension cord.

As generally discussed above, in some embodiments the plug may include electrical contacts that are capable of being simultaneously coupled with more than one receptacle. In some such embodiments, the plug may include contacts that may be capable of being simultaneously coupled with different electrical systems. For example, in an embodiment, the plug may include contacts that may be electrically coupled to an alternating current (AC) electrical receptacle (e.g., such as a NEMA 5-15 receptacle, or the like), and may also include contacts that may be electrically coupled to a direct current (DC) electrical receptacle (e.g., such as a 12 VDC power port or a USB port). In some such embodiments, the extension cord may include separate electrical conductors associated with the different electrical systems, as will be readily appreciated.

As generally discussed above, the extension cord 10 may be generally configured for providing transmission of power from a power source for remote usage by one or more electrical devices. In some embodiments, the power source may include a portable generator (e.g., portable generator 23, shown in FIGS. 4-5. In general, a portable generator may include an internal combustion engine driven generator. Further, a portable generator may generally include one or more electrical receptacles disposed on a control panel, housing, and/or chassis of the generator. Additionally, in some implementations, a portable generator may be manually portable, or portable via a cart, which may be integrated into a chassis of the generator (as by the inclusion of wheels. Portable generators may include a standard generator (e.g., which may provide a direct electrical output) and/or an inverter generator (e.g., which may process the output of the generator via a rectifier and inverter module, as is generally known). It will be appreciated that, while an extension cord consistent with the present disclosure may be used in connection with a portable generator, an extension cord consistent with the present disclosure may also suitably be used in connection with other types of generators (such as fixed generators), one or more batteries or battery banks (which could also include an inverter coupled with a battery bank, e.g., to provide AC power), an inverter associated with a vehicle (such as a recreation vehicle, a car, a truck, etc.), as well as various other power sources.

As shown in the illustrated example embodiments, consistent with the present disclosure, the outlet assembly 16 may be coupled with a second respective end of the plurality of electrical conductors (e.g., an may be physically coupled with the protective jacket 12). The outlet assembly 16 may include one or more outlet receptacles (e.g., outlet receptacles 18a-18f, which may also generally be referred to out "outlet receptacle 18") configured to provide electrical power from the power source (e.g., via the plug 12 and the electrical conductors) to one or more electrical devices that may be plugged into receptacles of the outlet assembly. The outlet assembly 16 may include one or more outlet receptacles 18. The outlet receptacles 18 may be capable of being electrically coupled with respective plugs of one or more electrical devices to be powered by the power source via the extension cord 10. The one or more outlet receptacles may include, but are not limited to, one or more of NEMA 5-15 receptacle, a NEMA 5-20 receptacle, a NEMA L14-30 receptacle, a 12 VDC power port socket, and a USB port. As shown in the illustrated example embodiments, in some implementations the outlet assembly may include a plurality of outlet receptacles. The plurality of outlet receptacles may include the same type of outlet receptacle (e.g., a plurality of NEMA 5-15 receptacles, a plurality of NEMA 5-20 receptacles, etc.), and/or may include more than one type of outlet receptacle (at least one NEMA 5-15 receptacle and at least one NEMA 5-20 receptacle, at least one NEMA 5-15 receptacle and at least one 12 VDC power port, at least one NEMA 5-15 receptacle and at least on USB port, as well as various other combinations of receptacles). In a similar manner as discussed with respect to the plug and a the protective jacket, one or more of the outlet receptacles may be outdoor rated.

As generally discussed above, the outlet assembly 16 may include a plurality of outlet receptacles 18, e.g., which may allow a plurality of devices to be plugged into the outlet assembly for receiving power from the power source via the extension cord 10. As shown, for example, in the illustrated example embodiments, the outlet assembly may include a plurality of receptacles which may be oriented in a variety of manners. For example, as shown in the illustrative example embodiment of FIG. 1, the outlet assembly 16a may include receptacles 18a, 18b, which may be spaced apart from one another, e.g., with one receptacle 18a being generally centrally located on the body of the outlet assembly 16a, and the other receptacle 18 being spaced therefrom and being generally disposed on the proximal end of the outlet assembly 16a. Consistent with such a configuration, it may be possible to connect multiple device plugs (i.e., a plug of a device plugged into the extension cord), including oversized device-plugs without interfering with one another (e.g., which may allow transformer-type device plugs to be coupled to either of the receptacles without interfering with adjacent device plugs, even other transformer-type device plugs). While not shown, an opposing side of the outlet assembly 16 a may include additional receptacles. In some embodiments, the additional receptacles may be offset from the receptacles 18a, 18b along the length of the outlet assembly 16a.

Referring also to the illustrative example embodiment of FIG. 2, another receptacle configuration of outlet assembly 16b is depicted. As shown, the outlet assembly 16b may include an array of receptacles 18c-18f. Consistent with the depicted embodiment, one of the receptacles (e.g., receptacle 18c) may be oriented differently from at least another receptacle (e.g., receptacles 18d-e), such that an oversized device plug (e.g., a transformer-type device plug) may be received in the receptacle 18c without interfering with adjacent device plugs, e.g., which may be received in one or more of receptacles 18d-e. Further, as shown, in addition to conventional AC receptacles, the outlet assembly 16b may include one or more receptacles having a different configuration. For example, outlet assembly 16b is shown including USB ports (e.g., USB port 18f), which may, for example, allow USB powered or charged devices to be electrically coupled to the outlet assembly 16b. In a configuration in which the outlet assembly includes one or more receptacles having a different output (e.g., a different voltage and/or a different current profile such as DC), the extension cord may include voltage supply circuitry (e.g., which may convert AC power provided by the power source to DC power and/or may change the voltage from the power supply to a desired output voltage) integrated into the plug and/or into the outlet assembly. In further embodiments, the extension cord may include a corresponding plug (e.g., a 12 VDC plug, a USB plug, etc.) that may be coupled with corresponding receptacles/ports of the power source, and may further include corresponding electrical conductors between the plug and the receptacles in the outlet assembly.

While particular types, numbers, and arrangements of receptacles have been shown, it will be appreciated that other configurations may also be utilized, depending upon design choice and preference. Accordingly, the depicted embodiments should be understood to be for the purpose of illustration and not limitation. Other receptacle types and arrangements should be understood as being encompassed by the present disclosure.

In some implementations, the outlet assembly 16 may be configured to bias one or more of the receptacles in an upward direction when the outlet assembly 16 is resting on a generally horizontal surface (such as the ground). Consistent with such a configuration, the openings of one or more of the receptacles may generally be oriented upwardly. Accordingly, if the outlet assembly is resting on a damp or wet surface ingress of moisture into openings of at least a portion of the one or more receptacles may be reduced and/or minimized. In some such implementations, a bottom surface (relative to the receptacle openings of one or more of the receptacles) may be weighted, enlarged, and/or otherwise configured to bias the openings of one or more outlet receptacles in an upward direction.

The outlet assembly 16 may further include a power meter configured to measure an electrical draw through the outlet assembly. For example, and referring also to FIG. 6, the outlet assembly 16 may include a controller 50, which may provide various functionality associated with the extension cord. For example, and with additional reference to FIG. 7, the controller (e.g., controller 50a) may provide a power meter configured, at least in part, to measure an electrical draw through the outlet assembly. Consistent with an illustrative example, the controller 50 (e.g., which may, at least in part, provide power meter functionality) may include a measurement subsystem 54, which may be configured to measure one or more of a current draw through the outlet assembly and a power draw through the outlet assembly. For example, and as is generally understood, the electrical draw through the outlet assembly may include the electrical power consumed by electrical devices that are plugged into the outlet assembly for receiving power from the power source via the extension cord. As is further generally understood, the electrical draw through the outlet assembly may be quantified in a variety of manners, include the current draw (i.e., the cumulative amperage—amps—of the electrical power being consumed by devices plugged into the receptacles of the outlet assembly at any given point in time) and power draw (i.e., the cumulative power—watts—of the electrical power being consumed by devices plugged into the receptacles of the outlet assembly at any given point in time). The power meter (e.g., including measurement subsystem 54) may utilize a variety of different circuitry and/or component assemblies, as are well understood in the art, to measure one or more of the current draw and/or the power draw through the outlet assembly.

The outlet assembly may further include a draw indicator (e.g., draw indicator 20, generally) that may be configured to provide a user perceptible indicator of the measured one or more of the current draw through the outlet assembly and the power draw through the outlet assembly. Accordingly, in some embodiments, draw indicator 20 may be coupled with controller 50a (e.g., which may include measurement subsystem 54) to facilitate providing the user perceptible indicator. For example, the draw indicator may provide a user perceptible indicator of a the measured current draw and/or power draw through the outlet assembly in absolute terms (e.g., a numerical value of the amps or watt being drawn through the outlet assembly) and/or in relative terms (e.g., a comparison of the current or power draw relative to a defined value, such as maximum rating of the extension cord, a maximum rating of the power source, a maximum rating of the power source receptacle(s) to which the plug 14 is coupled, and/or any other defined value).

Figure 3:
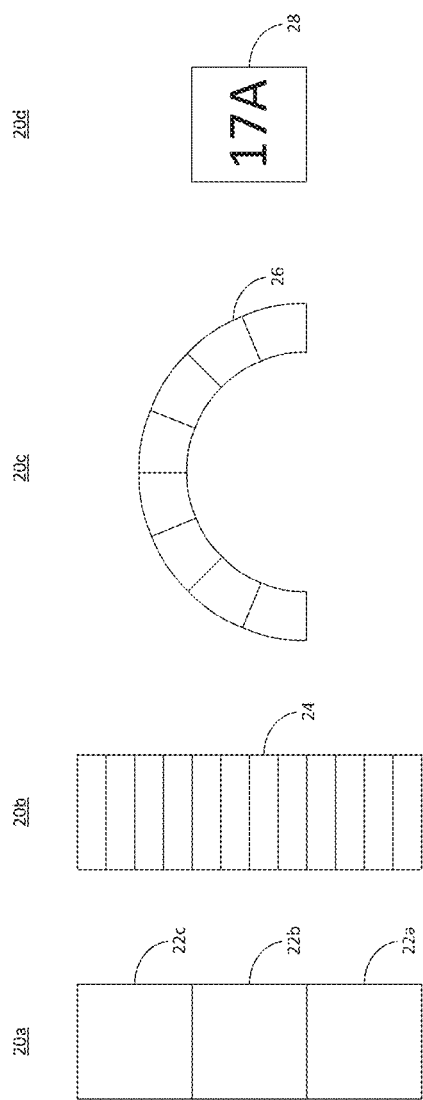
FIGS. 3A-3D depict various illustrative example embodiments of draw indicators that may be utilized in connection with an extensions cord consistent with an example embodiment.

It will be appreciated that a variety of user perceptible indicators may be utilized to provide a draw indicator. For example, in some embodiments, the user perceptible indicator may include one or more of a visual indicator and an auditory indicator. For example, and referring to FIGS. 3A-3D, several illustrative example draw indicators are shown. As shown in FIG. 3A, the draw indicator may include a relative indicator, e.g., which may include three segments (e.g., which may include LED's of the same or different color). Consistent with the illustrated embodiment, the draw indicator may include three segments 22a-c, which may each represent a relative draw through the outlet assembly. In some embodiments, the segments may be differently colored. For example, segment 22a may illuminate green when the draw is within a safe range (e.g., relative to a threshold such as a design maximum draw for the power source, the power source receptacle, the electrical conductors, the plug 14, the outlet assembly 16, the receptacles 18, etc.). Further, segment 22b may illuminate yellow, indicating a warning, as the draw approaches the threshold, and segment 22c may illuminate red when the draw reaches, or exceeds, the threshold. It will be appreciated that different colors may be used, and that the segments may cumulative illuminate (e.g., segment 22a is illuminated in the safe range, segments 22a and 22b may illuminate in the warning state, and segments 22a, 22b, and 22c may all illuminate when the threshold is reached or exceeded. It will be appreciated that other configurations may be utilized.

Referring to FIG. 3B, the draw indicator 20b may include a multi-segment display 24 (e.g., array of LED's, segments on an LCD display, etc.). The multi-segment display 24 may function progressively illuminate segments indicating progressively increasing draw through the outlet assembly. The various segments of the multi-segment display may be correlated to an absolute draw (e.g., with each segment representing a defined unit of draw, such as a defined number of amps or watts), and/or the multi-segment display may be correlated to a relative draw (e.g., relative to a threshold, as generally discussed above). Further, and referring to FIG. 3C, yet another draw indicator 20c is depicted having an arcuate configuration. The draw indicator 20c may include a segmented display 26, including segments that may be individually and/or cumulatively illuminated. The segmented display 26 may include any desired number of segments, and may operate in a manner generally as described with respect to draw indicator 20a and/or draw indicator 20b. Further, and referring to FIG. 3D, yet another illustrative example draw indicator 20d is depicted. As shown, draw indicator 20d may include a numerical display 28 (e.g., an LED numerical display, and LCD display, or other suitable display). The numerical display 28 may display a numerical value based upon the draw through the outlet assembly. The numerical value may indicate a value of the draw (e.g., the number of amps or watts being consumed through the outlet assembly) and/or may indicate a draw relative to a threshold (e.g., such as a percentage and/or relative to a defined numerical quantity such as 10, 5, etc.). It will be appreciated that numerical display 28 may provide other numerical quantifications of the draw through the outlet assembly.

Figure 4:
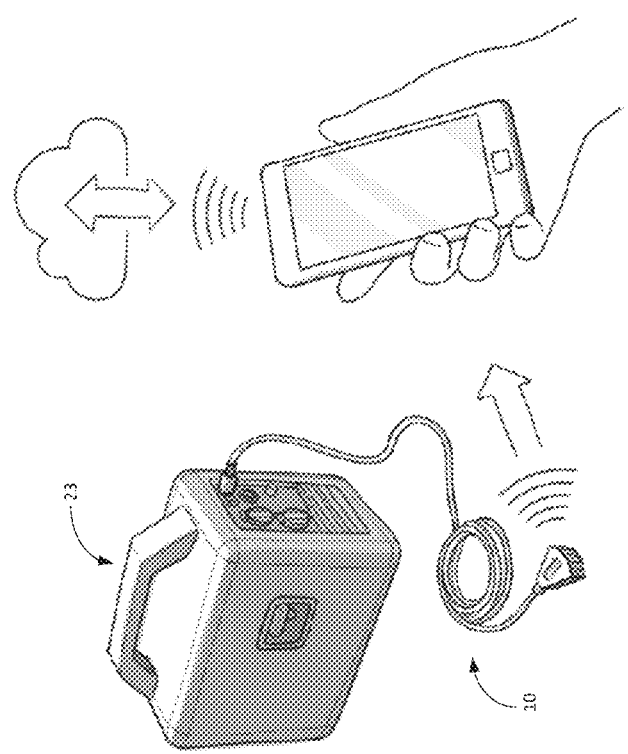
FIG. 4 depicts an illustrative example of an extension cord consistent with the present disclosure including a twist-lock plug, and including wireless communication, consistent with an example embodiment.

As shown, e.g., in FIGS. 4 and 5, in some embodiments the extension cord may include wireless communication capabilities. For example, the outlet assembly may include a wireless radio set (e.g., capable of Bluetooth, Wi-Fi, or other wireless communication functionality). Consistent with such an embodiment, the power meter may be configured to wirelessly transmit a draw indication to a cooperating device (such as a smartphone, a tablet, a smartwatch, a laptop, a special purpose device, or the like). The cooperating device may be configured to present a draw indication (e.g., either absolute and/or relative) via any suitable graphical user interface. Further, as discussed above, the draw indication may include an audible indicator, such as an alarm that may sound when a threshold draw is reached or exceeded.

In some embodiments, and as generally discussed above, the user perceptible indicator may be based upon, at least in part, a maximum service power associated with the plug. For example, and as also discussed above, the plug may include, but is not limited to, a NEMA 5-15 plug, a NEMA 5-20 plug, a NEMA L14-30 plug. As such, the plug may have a maximum current rating, and may be configured to be coupled with a receptacle having a corresponding maximum current rating. Further, in some embodiments the corresponding receptacle of the power source may include an overcurrent protection device (such as a circuit breaker) to prevent an excessive draw through the power source receptacle. As such, the thresholds associated with the draw indicator may be based upon, at least in part, the maximum current rating of a receptacle that the plug is configured to be coupled with. In one such example, the user perceptible indicator may provide at least an indication that the electrical draw through the outlet assembly is approaching a maximum service rating associated with the plug. For example, as discussed with regard to the illustrative example segmented draw indicators 20a-20c, the draw indicator may provide an escalating indication as the electrical draw through the outlet assembly approached (and/or exceeds) the current rating of the power source receptacle. Accordingly, the draw indicator may provide a user perceptible indication if the draw through the outlet assembly approaches or exceeds the current rating of the power source receptacle. Accordingly, if the electrical draw through the outlet assembly approaches (or exceeds) the maximum current rating of the power source receptacle, the draw indicator may provide an alert that may allow a user of the extension cord to take curative action (e.g., by discontinuing or modifying usage of one or more electrical devices plugged into the outlet assembly) before an overcurrent device associated with the power source receptacle trips. As such, the user may avoid having to move to the power source to reset the overcurrent device. This may be advantageous, for example, when the power source includes a portable generator that may be located outside of a building, and wherein the extension cord extends from the portable generator into the building where various electrical devices may be plugged into the outlet assembly. Additionally/alternatively, the draw indicator may provide the user of an awareness of the load being placed on the portable generator, e.g., which may allow the user to avoid overloading and/or overtaxing the portable generator.

Consistent with some implementations, an extension cord may include a carbon monoxide monitor. For example, in an illustrative example embodiment, an extension cord may include a plurality of electrical conductors, a plug configured to electrically couple a first respective end of the plurality of electrical conductors with an electrical receptacle of a power source, and an outlet assembly coupled with a second respective end of the plurality of electrical conductors, and including one or more outlet receptacles configured to provide electrical power from the power source, as generally discussed above. Additionally, in some embodiments consistent with the present disclosure, the outlet assembly may further include a carbon monoxide monitor configured to detect an environmental carbon monoxide level proximate the outlet assembly. The carbon monoxide monitor may be in addition to and/or as an alternative to the power meter described above. Accordingly, in some embodiments consistent with the present disclosure, an extension cord may include an outlet assembly including a power meter. In some embodiments consistent with the present disclosure an extension cord may include an outlet assembly including a carbon monoxide monitor. Further, in some embodiments consistent with the present disclosure, an extension cord may include an outlet assembly including a power monitor and including a carbon monoxide monitor.

Continuing with the foregoing, and referring also to FIG. 8, an illustrative embodiment of an outlet assembly may include a controller 50b (e.g., which may be a specific illustrative example implementation of the controller 50 shown in FIG. 6), which may include a carbon monoxide monitor 30, as schematically shown. For example, as shown, the outlet assembly may include a plurality of electrical conductors (e.g., electrical conductors 32, generally), which may be electrically coupled with one or more receptacles 18. The outlet assembly may further in the carbon monoxide monitor 30. The carbon monoxide monitor 30 may be configured to detect an environmental carbon monoxide level proximate the outlet assembly. That is, the carbon monoxide monitor 30 may be configured to detect a level (include detecting the presence of carbon monoxide above a threshold level) in the environment in proximity to the outlet assembly. For example, carbon monoxide may accumulate proximate the outlet assembly as a result of exhaust gasses from a generator (e.g., which may seep into a house or building in which the extension cord is being used (e.g., in which the outlet assembly may be in use to power various electrical devices). Similarly, carbon monoxide may accumulate and/or be present as a result of sources other than a generator.

In some embodiments consistent with the present disclosure, the carbon monoxide monitor may be configured to provide an alert when the detected environmental carbon monoxide level proximate the outlet assembly exceeds a threshold level. For example, the carbon monoxide monitor 30 may include a detection subsystem 34 that may detect a carbon monoxide level proximate the outlet assembly. The detection subsystem 34 may use any suitable known components or elements for detecting the carbon monoxide levels proximate the outlet assembly. Further, the carbon monoxide monitor 30 may include an evaluation subsystem 36, which may compare the detected carbon monoxide level relative to a defined threshold. The defined threshold may include any suitable threshold. In some embodiments, the defined threshold may include a carbon monoxide level above which individuals in proximity to the outlet assembly may experience adverse health effects. Further, in some embodiments, the carbon monoxide monitor 30 may include a communication subsystem 38, e.g., which may provide an alert when the carbon monoxide levels proximate the outlet assembly is at, or exceeds, the defined threshold. It should be appreciated that, while various subsystems have been individually identified, the various subsystems may be integrated into a single assembly, such as by being assembled on a common PCB or a common package. However, it will also be appreciated that one or more of the subsystems may be separate from one or more other subsystems. Further, one or more of the subsystems may be remote relative to one or more of the other subsystems.

As generally discussed above, in some embodiments consistent with the present disclosure, the carbon monoxide monitor may be configured to provide an alert when the detected environmental carbon monoxide level proximate the outlet assembly exceeds a threshold level. Accordingly, in some embodiments consistent with the present disclosure, the outlet assembly may include one or more of a visual alert unit and an audible alert unit for providing the alert when the detected environmental carbon monoxide level exceeds the threshold level. In some embodiments, the communication subsystem may include the alert unit. Consistent with the foregoing, in some example embodiments consistent with the present disclosure, the alert unit may include an audible alarm that may alert individuals proximate the outlet assembly that the carbon monoxide level exceeds the threshold level. In some embodiments consistent with the present disclosure, the alert unit may include an illuminated alert (such as a flashing LED, or other suitable visual alert) that may alert individuals proximate the outlet assembly that the carbon monoxide level exceeds the threshold. In some embodiments consistent with the present disclosure, the alert unit may provide both an audible alert and a visual alert that the carbon monoxide level exceeds the threshold.

As generally discussed above, in some embodiments, the power source may include a portable generator. Consistent with some such example embodiments, the carbon monoxide monitor may be operatively coupled with the portable generator (e.g., via the communication subsystem) to shut down an engine associated with the portable generator when the detected carbon monoxide level exceeds the threshold level. For example, in some illustrative embodiments, the portable generator may include a carbon monoxide monitor system that may be configured to shut down the engine of the portable generator when a detected carbon monoxide level proximate the portable generator exceeds a threshold level. However, as generally discussed above, an extension cord consistent with the present disclosure may allow devices to be powered by the portable generator even when such devices are relatively remote from the portable generator (e.g., by virtue of the length of the extension cord). For example, the portable generator may be located to operate outside of a house or building, and the extension cord may extend from the generator (located outside of the house or building) into the house or generator, and may allow devices to be plugged into the extension cord for use inside of the house or building. As such, the environment proximate the portable generator may be different from the environment proximate the outlet assembly of the extension cord. Accordingly, a situation may arise in which the carbon monoxide levels proximate the portable generator may be below the threshold level (e.g., may be at what is considered a safe level). However, carbon monoxide levels proximate the outlet assembly may exceed a safe level (e.g., may exceed a defined threshold). For example, exhaust gases from the portable generator may seep into the house or building and/or another source of carbon monoxide (either within the house or building and/or otherwise travelling into the house or building) may cause the carbon monoxide level proximate the outlet assembly to exceed a safe threshold.

In some implementations, an extension consistent with the present disclosure may be capable of communicating with the carbon monoxide monitor system of a portable generator to shut down the engine of the portable generator when a detected carbon monoxide level proximate the outlet assembly exceeds a threshold level. For example, the communication subsystem 38 of the carbon monoxide monitor 30 may be capable of communicating with the carbon monoxide monitor of the portable generator to cause the carbon monoxide monitor of the portable generator to shut down the engine. It will be appreciated that a variety of communication mechanisms may be utilized. For example, in one illustrative embodiment, the communication subsystem may utilize power line communication (PLC) to transmit a signal to the portable generator over one or more of the plurality of electrical conductors of the extension cord utilized to transmit power from the plug to the outlet assembly. Consistent with such an implementation, the portable generator may be configured to receive the PLC signal via a receptacle on the portable generator into which the plug of the extension cord is coupled. Upon receiving the signal from the extension cord, the carbon monoxide monitor of the portable generator may shut down the engine. It will be appreciated that other wireline communication protocols (including wireline communication protocols using electrical conductors other than the plurality of electrical conductors utilized for transmitting electrical power via the extension cord) may also suitable be utilized. Additionally and/or alternatively, the communication subsystem may utilized wireless communication functionality (e.g., Bluetooth, Wi-Fi, or other suitable wireless communication functionality, either directly communicating with a control system of the portable generator and/or indirectly communicating with a control system of the portable generator, as via a wireless device, such as a smartphone, etc.) to communicate with the portable generator (e.g., a control system of the portable generator) to shut down the engine if a carbon monoxide level proximate the outlet assembly exceeds a defined threshold. Consistent with such embodiments, the carbon monoxide monitor may be communicatively coupled with a control system of the portable generator to shut down the engine. It should be appreciated that in some embodiments, the carbon monoxide monitor of the extension cord may augment the carbon monoxide safety system of the portable generator (e.g., rather than replacing it). As such, a control system of the portable generator may be configured to shut down the engine if the carbon monoxide safety system of the portable generator detects a carbon monoxide level proximate the portable generator exceeding a threshold, and the control system of the portable generator may be configured to shut down the engine if the carbon monoxide monitor of the extension cord detects a carbon monoxide level proximate the outlet assembly exceeding a threshold.

In some embodiments consistent with the present disclosure, the extension cord may be configured to shut down the engine of a portable generator, in response to detecting a carbon monoxide level proximate the outlet assembly exceeding a threshold level, even if the portable generator is not equipped with a carbon monoxide safety system. For example, in some embodiments, the extension cord may include a shutdown module 40 that may be disposed proximate the portable generator. The shutdown module may be capable of receiving a signal (e.g., a wireline signal, such as using PLC protocol or another suitable wireline signal, a wireless signal, for example via Bluetooth, Wi-Fi, or another suitable wireless signal) from the carbon monoxide monitor of the extension cord. The shutdown module 40 may be operatively coupled with the engine of the portable generator to shut down the engine when a signal is received indicating a carbon monoxide level proximate the outlet assembly exceeds a threshold. For example, the shutdown module may wired into an off switch of the engine, a low oil shutdown switch, and/or another mechanism of the engine that may effectuate shutdown of the engine.

According to various embodiments, an extension cord consistent with the present disclosure may include various additional and/or alternative features. For example, in some embodiments the extension cord may be configured to detect a sudden change in the power output received from the power source, such as a portable generator. For example, the extension cord (e.g., the controller 50 of the outlet assembly) may be configured to detect a loss of power being provided to the extension cord. Such a loss of power being provided to the extension cord may indicate that the extension cord has been unplugged from the power source, e.g., as may occur if the cord is unplugged cut as part of an attempted theft of the portable generator, as a result of an accident (e.g., an individual tripping over the cord, etc.), tripping of an overcurrent protection device associated with the portable generator, a mechanical and/or electrical problem with the generator (e.g., the engine running out of fuel, a low oil sensor causing a shutdown of the engine, etc.). Upon detecting such a loss in power provided from the power source (e.g., portable generator), the controller may provide a visual and/or an audible alert (either directly and/or via a communicatively coupled device, such as a smartphone, or the like) to notify a user of the sudden loss of power from the power source. In this regard, in some embodiments, the extension cord may include an auxiliary power source 52 (such as a rechargeable battery, a capacitor/super capacitor, etc.) which may provide at least temporary power to the controller and/or any alert features (such as an audible alarm, a visual alert, a wireless communication module, etc.).

As generally discussed above, and as shown, e.g., in FIGS. 4-5, in some embodiments consistent with the present disclosure, an extension cord may provide remote device connectivity (e.g., via wired or wireless communication with a remote device such as a smartphone, a smartwatch, a tablet, a laptop, a special purpose device, etc.). Consistent with such an implementation, an extension cord may provide a variety of information to a user and/or to a remote repository (e.g., a network accessible database or the like associated with a manufacturer of the extension cord or portable generator, and/or another third party). Examples of such information may include, but are not limited to, electrical draw through the extension cord, carbon monoxide levels proximate the outlet assembly, a number of devices connected to the outlet assembly, generator information (such as runtime, current or historical operating information, service information, etc.), as well as a variety of other information. In some embodiments, such as when information pertaining to the generator are provided, such information may be gathered from the generator via a suitable communication arrangement, such as a wired communication arrangement (e.g., PLC or another suitable wired communication protocol) or a wireless communication arrangement (e.g., Bluetooth, Wi-Fi, or another suitable wireless communication protocol).

While the present disclosure has generally been described in the context of an extension cord for a portable generator, such description has been presented for the purpose of illustration. It will be appreciated that an extension cord consistent with the present disclosure may be utilized for a variety of purposes. As such, the present disclosure is considered to be broadly directed at any electricity outlet application.

A variety of features of the have been described herein. However, it will be appreciated that various additional features and structures may be implemented in connection with an extension cord according to the present disclosure. Further, additional features and details may be depicted in the figures that may not explicitly be described in the detailed description. However, such features and details should be understood as being included within the scope of the present disclosure. Additionally, the various features described herein may be implemented in a variety of combination and sub-combination, including less than all of the described features, and/or some or all of the described features in combination will additional features not specifically detailed in the present disclosure. As such, the features and attributes described herein should not be construed as a limitation on the present disclosure.

What is claimed is:

1. An extension cord comprising:
a plurality of electrical conductors;
a plug configured to electrically couple a first respective end of the plurality of electrical conductors with an electrical receptacle of a power source;
an outlet assembly coupled with a second respective end of the plurality of electrical conductors, the outlet assembly including one or more outlet receptacles configured to provide electrical power from the power source, the outlet assembly further including a power meter configured to measure an electrical draw through the outlet assembly, wherein the outlet assembly further includes a draw indicator providing a visually perceptible indicator of the electrical draw through the outlet assembly relative to a maximum draw associated with the plug;
wherein the power source includes a portable generator, and wherein the outlet assembly includes a carbon monoxide monitor communicatively coupled with the portable generator to shut down the portable generator when an environmental carbon monoxide level proximate the outlet assembly exceeds a threshold level.

2. The extension cord according to claim 1, wherein the power source includes a portable generator.

3. The extension cord according to claim 1, wherein the plug includes one or more of a NEMA 5-15 plug, a NEMA 5-20 plug, a NEMA L14-30 plug, a 12 VDC power port plug, and a USB plug.

4. The extension cord according to claim 1, wherein the one or more outlet receptacles include one or more of NEMA 5-15 receptacle, a NEMA 5-20 receptacle, a NEMA L14-30 receptacle, a 12 VDC power port socket, and a USB port.

5. The extension cord according to claim 1, wherein the power meter is configured to measure one or more of a current draw through the outlet assembly and a power draw through the outlet assembly.

6. The extension cord according to claim 1, wherein the user perceptible indicator includes one or more of a visual indicator and an auditory indicator.

7. The extension cord according to claim 1, wherein the user perceptible indicator provides at least an indication that the electrical draw through the outlet assembly is approaching a maximum service rating associated with the plug.

8. The extension cord according to claim 1, wherein the outlet assembly further includes a carbon monoxide monitor configure to detect an environmental carbon monoxide level proximate the outlet assembly and to provide an alert when the detected environmental carbon monoxide level proximate the outlet assembly exceeds a threshold level.

9. An extension cord comprising:
a plurality of electrical conductors;
a plug configured to electrically couple a first respective end of the plurality of electrical conductors with an electrical receptacle of a power source;
an outlet assembly coupled with a second respective end of the plurality of electrical conductors, the outlet assembly including one or more outlet receptacles configured to provide electrical power from the power source, the outlet assembly further including a carbon monoxide monitor configured to detect an environmental carbon monoxide level proximate the outlet assembly, wherein the power source includes a portable generator including a portable generator carbon monoxide monitor system configured to shut down an engine of the portable generator, and wherein the outlet assembly carbon monoxide monitor is communicatively coupled with the portable generator carbon monoxide monitor system to shut down the portable generator when the environmental carbon monoxide level proximate the outlet assembly exceeds a threshold level.

10. The extension cord according to claim 9, wherein the power source includes a portable generator.

11. The extension cord according to claim 9, wherein the plug includes one or more of a NEMA 5-15 plug, a NEMA 5-20 plug, a NEMA L14-30 plug, a 12 VDC power port plug, and a USB plug.

12. The extension cord according to claim 9, wherein the one or more outlet receptacles include one or more of NEMA 5-15 receptacle, a NEMA 5-20 receptacle, a NEMA L14-30 receptacle, a 12 VDC power port socket, and a USB port.

13. The extension cord according to claim 9, wherein the carbon monoxide monitor is configured to provide an alert when the detected environmental carbon monoxide level proximate the outlet assembly exceeds the threshold level.

14. The extension cord according to claim 13, wherein the outlet assembly includes one or more of a visual alert unit and an audible alert unit for providing the alert when the detected environmental carbon monoxide level exceeds the threshold level.

15. The extension cord according to claim 9, wherein the outlet assembly further includes a power meter configured to measure an electrical draw through the outlet assembly and to provide a user perceptible indication based upon the measured electrical draw.

16. An extension cord comprising:
a plurality of electrical conductors;
a plug configured to electrically couple a first respective end of the plurality of electrical conductors with an electrical receptacle of a power source;
an outlet assembly coupled with a second respective end of the plurality of electrical conductors, the outlet assembly including:
one or more outlet receptacles configured to provide electrical power from the power source;
a power meter configured to measure an electrical draw through the outlet assembly and to provide a user perceptible output based upon the measured electrical draw;
a carbon monoxide monitor configured to detect an environmental carbon monoxide level proximate the outlet assembly and to provide a user perceptible indication when the detected environment carbon monoxide level exceeds a threshold; and a controller, coupled with an auxiliary power source, configured to detect a loss of power from the power source and to provide an alert indicative of the loss of power;

wherein the power source includes a portable generator, and wherein the outlet assembly includes a carbon monoxide monitor communicatively coupled with the portable generator to shut down the portable generator when an environmental carbon monoxide level proximate the outlet assembly exceeds a threshold level.

* * * * *